United States Patent
Bergmann et al.

(10) Patent No.: US 8,124,366 B2
(45) Date of Patent: Feb. 28, 2012

(54) METHOD FOR THE DETERMINATION OF THE FORMATION OF ENDOTHELINS FOR MEDICAL DIAGNOSTIC PURPOSES, AND ANTIBODIES AND KITS FOR CARRYING OUT SUCH A METHOD

(75) Inventors: Andreas Bergmann, Berlin (DE); Joachim Struck, Berlin (DE)

(73) Assignee: B.R.A.H.M.S. GmbH, Hennigsdorf (DE)

( * ) Notice: Subject to any disclaimer, the term of this patent is extended or adjusted under 35 U.S.C. 154(b) by 974 days.

(21) Appl. No.: 10/588,746

(22) PCT Filed: Feb. 10, 2005

(86) PCT No.: PCT/EP2005/001359
§ 371 (c)(1),
(2), (4) Date: May 23, 2007

(87) PCT Pub. No.: WO2005/078456
PCT Pub. Date: Aug. 25, 2005

(65) Prior Publication Data
US 2008/0026414 A1     Jan. 31, 2008

(30) Foreign Application Priority Data
Feb. 13, 2004  (EP) .................................... 04003295

(51) Int. Cl.
*G01N 33/00* (2006.01)
(52) U.S. Cl. ........ 435/7.94; 435/7.1; 435/7.92; 436/518
(58) Field of Classification Search .................. None
See application file for complete search history.

(56) References Cited

U.S. PATENT DOCUMENTS
6,756,483 B1   6/2004  Bergmann et al. ............ 530/399

FOREIGN PATENT DOCUMENTS
WO   WO 00/22439   4/2000

OTHER PUBLICATIONS

Kuriyama et al., Monoclonal Anti-Dideptide Antibodies Cross-React with Detyrosinated and Glutamylated Forms of Tubulins, Cell Motility and the Cytoskeleton 30: pp. 171-182, 1995.*
Kido et al., Processing of proendothelin-1 at the C-terminus of bigh endothelin-1 is essential for proteolysis by endothelin-converting enzyme-1 in vivo, Eur. J. Biochem. 244, 1997, pp. 520-526.*
Hemsen A. et al., "Metabolism of Big endothelin-1 (1-38) and (22-38) in the human circulation in relation to production of endothelin-1 (1-21)" Regulatory Peptides 1995 Netherlands, vol. 55, No. 3, 1995, pp. 287-297.

* cited by examiner

*Primary Examiner* — Melanie J Yu
*Assistant Examiner* — Gary W Counts
(74) *Attorney, Agent, or Firm* — Heslin Rothenberg Farley & Mesiti P.C.

(57) ABSTRACT

The invention relates to an in vitro method for detecting the formation of endothelins during serious illnesses, especially cardiovascular diseases, inflammations, sepsis and cancer, in whole blood, plasma or serum of a human patient for medical diagnosis. Using this method, relatively long-lasting peptide fragments, especially a C-terminal peptide fragment, of the processed primary prepro- or proendothelins that contain neither the actual biologically active endothelin nor its direct precursor, big endothelin, can be detected.

15 Claims, 4 Drawing Sheets

METHOD FOR THE DETERMINATION OF THE FORMATION OF ENDOTHELINS FOR MEDICAL DIAGNOSTIC PURPOSES, AND ANTIBODIES AND KITS FOR CARRYING OUT SUCH A METHOD

CROSS REFERENCE TO RELATED APPLICATIONS

This application is a U.S. national stage filing under 35 U.S.C. §371 U.S. of PCT Application Ser. No. PCT/EP2005/001359 having an international filing date of Feb. 10, 2005, published in German under Publication No. WO 2005/078456 A1 on Aug. 25, 2005, which claims priority from European Application Ser. No. EP 04003295.5, filed Feb. 13, 2004; the disclosures of these applications are hereby incorporated by reference in their entirety.

FIELD OF THE INVENTION

The invention relates to methods for the determination of the formation of endothelins in serious diseases by determining peptide fragments of the corresponding proendothelin, in particular a relatively long-lived C-terminal partial peptide of preproendothelin-1, in the circulation (whole blood, plasma or serum) for medical diagnostic purposes, in particular in sepsis diagnosis, in cardiac diagnosis and, for example, also in cancer diagnosis and/or generally in the diagnosis of those pathological conditions in which endothelins play an important role for the course of the disease.

Where simply the term "endothelin" is used in the present Application, this term primarily represents endothelin-1 (ET-1). However, a corresponding statement is frequently also applicable to other isoforms of endothelins, and therefore a limitation to endothelin-1 frequently appears unnecessary and the invention is also intended to include other endothelins in a wider sense.

In this description, the term "diagnostic" is used in principle as a simplifying general term which is intended to include in particular prognosis/early prognosis and therapy-accompanying monitoring.

The determinations are effected in particular by means of specific immunodiagnostic methods, in particular by means of immunoassays of a type in which at least one marked antibody is employed (sandwich assay; competitive assay, e.g. according to the SPALT or SPART principle).

BACKGROUND OF THE INVENTION

Endothelin-1 (ET-1), a peptide comprising 21 amino acids, is the strongest known vasoconstrictor. Since its discovery in 1988 by Yanagisawa et al. [27; numerical data in square brackets relate to the attached list of references], biosynthesis, mode of action and association with diseases have been comprehensively investigated and summarized in topical review articles [1, 7, 12, 17, 24]. There are three isoforms of endothelin which are coded by different genes (endothelin-1, endothelin-2, endothelin-3) of which endothelin-1 is present in the greatest concentrations and is the most effective. Endothelin-1 is synthesized in endothelium cells, in the lung, in the heart, in the kidney and in the brain. The primary translation product of the human endothelin-1 gene is a peptide comprising 212 amino acids, preproendothelin-1 (SEQ ID NO: 1). In the secretion process, a short N-terminal signal sequence (amino acids 1-17) of the preproendothelin is removed by the signal peptidase. The proendothelin obtained is then processed by the protease furin on dibasic amino acid pairs to give a biologically inactive peptide comprising 38 amino acids, big endothelin (SEQ ID NO:3), from which finally the mature, biologically active endothelin-1 (SEQ ID NO:2) is formed by means of endothelin-converting enzymes (ECEs). Endothelin acts via the bond to specific receptors which are localized on muscle cells, myocytes and fibroblasts. This bond leads to efflux of calcium, activation of phospholipase C and inhibition of Na/K ATPase. In addition to the vasoconstrictive effect, endothelin also has growth-regulating properties.

In view of the detectable and presumably numerous and serious physiological effects of endothelins, in particular endothelin-1, various assays for its immunodiagnostic determination have been developed since the time of its identification and have been used for measurements of endothelin(s), in particular in human plasmas. The results of such determinations are the subject of numerous publications.

Raised plasma concentrations of endothelin-1 and big endothelin have been described for various clinical pictures [17]. These include cardiovascular diseases [1] (inter alia pulmonary hypertension [21], atherosclerosis [13], congestive heart failure [25], myocardial infarction [20]), sepsis and septic shock [11, 22, 23], cancer [2, 3, 15, 18], etc.

The immunoassays used for the measurements of endothelins in plasma samples (cf. the review in [17]) belonged in particular to the radioimmunoassay type (with marked endothelin-1 as competitor) or to the EIA/ELISA type and aimed exclusively at the determination of endothelin or the determination of an endothelin immunoreactivity. Assays of the RIA type have low specificity and also determine related peptides containing the endothelin sequence.

However, it was found that endothelin-1 (ET-1) has an extremely short residence time in the circulation and that it is removed from the circulation after only 1-2 min [6]. Since endothelin-1 in blood and plasma is considered to be stable [6], its distribution in other tissue and its rapid and high-affinity bonding to receptors are regarded as the most important reason for the short residence time. In certain tissues and body fluids, substantially higher endothelin-1 concentrations than, for example, in plasma could consequently be determined [1, 7]. In view of these circumstances, serious doubt was cast on the validity of the determination of ET-1 in plasma samples [17]. It is in fact to be assumed that the instantaneous ET-1 concentrations determinable in a plasma sample and reflecting in certain circumstances only a transition state are not important for the physiological effects of endothelin (ET-1) but that the sum of all free and bound, e.g. tissue- and receptor-bound, physiological ET-1 concentrations present in the organism are of much greater relevance.

The determination of the ET-1 precursor, of so-called big endothelin ("big ET-1"; SEQ ID NO:3), has the advantage over the determination of ET-1 that the residence time of "big ET-1" in the circulation is substantially longer than that of the ET-1 liberated therefrom. In a number of investigations, this "big endothelin" was therefore determined instead of the actual endothelin. In particular assays of the sandwich type which permit a reliable distinction of big endothelin-1 from processed ET-1 and other endothelins were used for its specific determination [4, 8, 10]. They showed that, in certain diseases, the increased ET immunoreactivities measured can be attributed to big ET.

The selective measurement of big-ET-1 represents only a gradual improvement but not an actual solution to the problem, since big endothelin too can be processed rapidly in blood circulation to give endothelin [1, 5, 9]. It therefore likewise has a relatively short biological half-life (20-25 minutes) [10], and consequently a measured value of the big endothelin determinable in the plasma likewise represents only an instantaneous plasma concentration and does not reflect the actual physiologically effective concentrations of endothelin. ET-1 formed physiologically under the conditions of a disease but already processed and bound into tissues or to receptors is not detected in plasma in the determination of big-ET-1. The total amount of physiologically active endothelin is therefore also underestimated in a measurement of big endothelin. An attempt to perform a supplementary specific measurement of the C-terminal peptide fragment of big-ET-1 (with the amino acids 74-90 of preproendothelin or the amino acids 20-38 of big endothelin) formed in the enzymatic cleavage of big-ET-1 in addition to ET-1 showed that this peptide is even less stable than ET-1 and is therefore unsuitable for measurements [10].

The prior art discloses only one commercial competitive test (N-terminal range 18-50, commercially available from Phoenix Pharmaceuticals; use for the sepsis diagnosis described in WO 00/22439) for evaluating ranges of proendothelin outside that of big endothelin. No information has been published regarding the stability and nature of the analyte to be evaluated using this assay.

It is the object of the present invention to develop an assay method which reflects the endogenous formation of big endothelin and endothelin, i.e. the total physiological concentration and hence action of endothelin, more reliably than the determinations to date of ET or big ET in plasma.

Such a method should be valid and capable of routine use and should be capable of providing reliable values for the physiological production of ET (ET-1) and/or its precursors in various pathological conditions, in particular in sepsis or other pathological conditions in which increased values for endothelin play a role.

SUMMARY OF THE INVENTION

This object is achieved, according to the invention, by determining not ET or big ET but a comparatively long-lived prepro- or proendothelin partial peptide which does not contain the ET or big ET sequences, in particular a C-terminal partial peptide which contains at least the amino acids 168-212 of pre-proET-1, in a whole blood, plasma or serum sample of a human patient, for diagnostic purposes.

The invention is based on experimental investigations by the Applicant in which said Applicant was able to show that those parts of preproendothelin which do not represent direct precursors of endothelin comprise long-lived peptides which are suitable for measuring purposes and can be measured in blood samples reliably and with a high clinical relevance.

Endothelin-1 is formed physiologically by processing of the larger precursor molecule preproendothelin (SEQ ID NO:1) or of the secreted proendothelin obtained therefrom. During such processing, further peptides form in primarily stoichiometric amounts in addition to big endothelin (and therefrom endothelin), which further peptides, however, have to date not been the subject of scientific investigations and about whose possible further processing and stability nothing has been disclosed to date. At the beginning of the investigations by the Applicant, it was hoped that it would be possible to show that at least one of the hypothetical further peptide cleavage products is present in blood samples (whole blood, plasma or serum samples) and would prove to be relatively stable and which cleavage product might therefore be suitable to serve as a measure of the physiological formation of endothelins independently of an endothelin concentration actually measurable in plasma.

The evaluation of such a cleavage product might therefore represent the method sought for the determination of the physiological endothelin concentration or production which is designated in the Claims as determination of the "formation of endothelins". This term is used to refer to the fact that—assuming only one route of formation, namely the single known route of formation, of endothelin-1 from proendothelin—the physiological concentrations of endothelin 1 which are formed in association with the disease can correspond only to the amount of the previously processed preproendothelin or proendothelin. If the partial peptides formed in the same stoichiometric concentration in addition to big endothelin or endothelin are stable "metabolic waste products" which are neither bound to receptors nor distributed in tissues, they must be present in the circulation. Without wishing thereby necessarily to imply a certain physiological mechanism, the "determination or measurement of the formation of endothelins" can therefore also be regarded as measurement "of the secretory activity" or of the "secretory proendothelin production".

In this Application, the peptide fragments to be determined are characterized as "long-lived". This term means that the residence time of the peptide fragment to be determined in the circulation (in whole blood) is considerably longer than that of endothelin or of big endothelin fragments. In particular, "long-lived" means that such peptide fragments in whole blood or a plasma obtained therefrom are not subject to further rapid proteolytic cleavage and, compared with the rate of binding of endothelin to receptors and of proteolytic cleavage of cleavable fragments, are removed at a substantially slower rate from the circulation or the metabolism.

Owing to said longer stability or "long-lived character", in the presence of such fragments the information relating to the already elapsed secretory activities is stored for a period which is suitable at least for an unproblematic measurement. If it is assumed, for example, that the endothelin precursors are liberated in a single short-term secretion, the amount of "long-lived" fragments which are measurable after a certain time corresponds to the originally secreted amount, reduced only by an amount which is linked to the physiological half-life of the peptide fragment to be measured in the circulation. If on the other hand, for example, a more or less continuous production of the endothelin precursor during the pathological process is assumed, the former physiological production of the precursor is cumulatively reflected in the measurable concentration of a peptide fragment which is long-lived in the above sense, once again reduced only by the concentration reduction of the peptide fragment which has taken place in the same period, in accordance with its physiological clearance rate. The active endothelin or its precursor big endothelin may have long been processed or removed from the circulation in the same period and, for example, may be bound to receptors and therefore no longer measurable. The longer lived a peptide fragment is or the lower its clearance rate, the smaller is the influence of the time of measurement on the correctness of the determination of the abovementioned "formation" of a biomarker, i.e. of endothelin. A concentration constant over a relatively long period means in this context that formation and clearance hold the balance. If the concentration decreases, this may indicate that the secretion of the precursor molecule (for example of proendothelin) has ceased, for example because the molecular reservoirs are exhausted, and the concentration changes to be observed are determined only by the clearance rate.

The results of the measurement of a long-lived peptide fragment without known physiological function thus provides both quantitatively and qualitatively different results from a measurement of a fairly short-lived active peptide or its likewise relatively short-lived precursor.

The investigations by the Applicant which are described in more detail below showed that the approach described above gives fruitful results in the case of the determination of the formation of endothelins.

BRIEF DESCRIPTION OF THE DRAWINGS

The investigations carried out and the most significant results of the investigations are explained more exactly below, reference being made to figures. In the figures.

DETAILED DESCRIPTION OF THE INVENTION

The method according to the invention relates in its most general aspect to the determination of a relatively long-lived peptide fragment of proendothelin-1 which does not contain the amino acid sequences of endothelin-1 or its precursor big endothelin, in whole blood, plasma or serum samples, i.e. in the circulation of patients, for the indirect determination of the formation of endothelins, in particular of endothelin-1, in serious diseases. According to a preferred embodiment, the peptide fragment determined is a C-terminal fragment to which two antibodies bind which bind to peptides having amino acid sequences which correspond to the positions 168-181 and 200-212 of preproendothelin-1.

For the practical implementation of the invention, noncompetitive sandwich assays, for example of the type as used for the more far-reaching detailed investigations and described more exactly below, are particularly preferably provided.

Compared with competitive immunoassays, noncompetitive sandwich immunoassays (two-sided immunoassays) have a number of advantages, which include the fact that they can be better designed than solid-phase assays (heterogeneous assays), may be more rugged in terms of handling, can give measured results with a higher sensitivity and are also more suitable for automation and series measurement. Moreover, they can also provide additional information compared with competitive immunoassays which operate with only one type of antibody, in that sandwich immunoassays recognize only those molecules or peptides with which both binding sites for the antibodies used in the sandwich formation are present on the same molecule.

The antibodies which may be used may in principle be any desired suitable monoclonal and/or polyclonal antibodies, but affinity-purified polyclonal antibodies are currently preferred.

Particularly preferably, the antibodies are obtained by immunization of an animal, in particular of a sheep, with an antigen which contains a synthetic peptide sequence which corresponds to a short amino acid sequence of preproendothelin-1 and an additional cysteine residue at the N-terminus. In the following experimental section, in particular antibodies which bind to the amino acid sequences 161-181 and 200-212, and their use in an assay are described. However, in the course of the investigations, additional antibodies which accordingly bind to the positions 184-203 and 136-148 were also used. The additional results obtained with these further antibodies in measurements are discussed only globally in this Application.

In a preferred embodiment, the method is carried out as a heterogeneous sandwich immunoassay, in which one of the antibodies is immobilized on any desired solid phase, for example the walls of coated test tubes (e.g. of polystyrene; "coated tubes"; CT) or on microtiter plates, for example of polystyrene, or on particles, for example magnetic particles, while the other antibody carries a residue which represents a directly detectable label or permits selective linkage to a label and serves for detecting the sandwich structures formed. Delayed or subsequent immobilization with the use of suitable solid phases is also possible.

In principle, all marking techniques which can be used in assays of the type described may be employed, including marking with radioisotopes, enzymes, fluorescent, chemiluminescent or bioluminescent labels and directly optically detectable color markers, such as, for example, gold atoms and dye particles, as are used, in particular for so-called point-of-care (POC) or accelerated tests for determination in whole blood samples. In the case of heterogeneous sandwich immunoassays, the two antibodies may also have parts of a detection system of the type described below in relation to homogeneous assays.

It is therefore within the scope of the present invention also to design the method according to the invention as an accelerated test.

The method according to the invention can furthermore be designed as a homogeneous method in which the sandwich complexes formed from the two antibodies and the peptide fragment to be detected remain suspended in the liquid phase. In such a case, it is preferable to mark both antibodies with parts of a detection system which permits signal generation or signal triggering when both antibodies are integrated into a single sandwich. Such techniques can be designed in particular as fluorescence amplification or fluorescence extinction assays. A particularly preferred method of this type relates to the use of detection reagents to be used in pairs, as described, for example, in U.S. Pat. No. 4,822,733, EP-B1-180 492 or EP-B1-539 477 and the prior art cited therein. They permit a measurement which selectively detects only reaction products which contain both marking components in a single immune complex, directly in the reaction mixture. The technology which is available under the brands TRACE® (Time Resolved Amplified Cryptate Emission) and KRYPTOR® and which implements the teachings of the above-mentioned application may be referred to as an example.

In the investigations by the Applicant, it was found that the determination, according to the invention, of the C-terminal peptide fragment of preproendothelin-1 gives highly interesting and relevant results. As will be shown below, this statement applies not only to the sepsis diagnosis but also to cardiac diagnosis and cancer diagnosis.

It is furthermore assumed that the assays according to the invention can also be particularly advantageously carried out as part of a so-called multiparameter diagnosis, in particular both in the area of cardiac diagnosis and in sepsis and cancer diagnosis. Further parameters determined thereby are, for example, the cardiac parameters ANP, BNP, proANP, proADM and proBNP or sepsis parameters which are selected, for example, from the group which consists of anti-ganglioside antibodies, the proteins procalcitonin, CA 125, CA 19-9, S100B, S100A proteins, LASP-1, soluble cytokeratin fragments, in particular CYFRA 21, TPS and/or soluble cytokeratin-1 fragments (sCY1F), the peptides inflammin and CHP, other peptide prohormones, glycine-N-acyltransferase (GNAT), carbamoylphosphate synthetase 1 (CPS 1) and C-reactive protein (CRP) or fragments thereof. In said multiparameter assays, it is intended to determine the measured results for a plurality of parameters simultaneously or in parallel and to evaluate them, for example, with the aid of a computer program which also uses diagnostically significant parameter correlations.

The invention is explained in more detail below by a description of the preparation of the preferred assay components, the procedure of a preferred embodiment of an assay of the sandwich type and the results of the determination of a C-terminal peptide fragment in EDTA plasmas of control persons and of sepsis, cardiac and cancer patients, obtained with the use of such an assay.

Experimental Section
A. Materials and Methods
1. Peptide Syntheses

Derived from the known amino acid sequence of human preproendothelin-1 (SEQ ID NO:1), three ranges were selected (Pos. 168-181, 184-203, 200-212). In each case supplemented by an N-terminal cysteine residue, these ranges were chemically synthesized as soluble peptides by standard methods, purified, quality-controlled by means of mass spectrometry and reversed phase HPLC and lyophilized in aliquots (JERINI AG, Berlin, Germany). The amino acid sequences of the peptides are:

```
Peptide PCT15            (168-181 + N-terminal
CRSSEEHLRQTRSET          cysteine)
                         (SEQ ID NO:4)

Peptide PCW14            (200-212 + N-terminal
CSRERYVTHNRAHW           cysteine)
                         (SEQ ID NO:5)

Peptide PNR20            (184-203 + N-terminal
NSVKSSFHDPKLKGKPSRER     cysteine)
                         (SEQ ID NO:6)
```

Furthermore, the following peptide was synthesized as a standard for calibrating the assays:

```
  Standard peptide PSW44 (169-212)
                                       (SEQ ID NO:7)
  SSEEHLRQTRSETMRNSVKSSFHDPKLKGKPSRERYVTHNRAHW
```

2. Conjugation and Immunization

The peptides PCT15 and PCW14 were conjugated with the carrier protein KLH (keyhole limpet hemocyanine) by means of MBS (m-maleimidobenzoyl-N-hydroxysuccinimide ester) (cf. operating instructions "NHS-Esters-Maleimide Crosslinkers", from PIERCE, Rockford, Ill., USA). Sheep were immunized with these conjugates according to the following scheme: each sheep initially received 100 μg of conjugate (stated mass based on the peptide fraction of the conjugate) and then 50 μg portions of conjugate every 4 weeks (stated mass based on the peptide fraction of the conjugate). Beginning with the fourth month after beginning of the immunization, 700 ml of blood per sheep were taken every 4 weeks and antiserum was obtained therefrom by centrifuging. Conjugations, immunizations and recovery of antisera were carried out by MicroPharm, Carmarthenshire, UK.

3. Purification of the Antibodies

The peptide-specific antibodies were prepared in a one-step method from the antisera which had been recovered beginning with the fourth month after immunization.

For this purpose, the peptides PCT15 and PCW14 were first coupled to SulfoLink Gel (cf. operating instruction "SulfoLink Kit", from PIERCE, Rockford, Ill., USA). In each case 5 mg of peptide per 5 ml of gel were offered for coupling.

The affinity purification of peptide-specific antibodies from sheep antisera against both peptides was carried out as follows:

The peptide columns were first washed three times alternately with 10 ml each of elution buffer (50 mM citric acid, pH 2.2) and binding buffer (100 mM sodium phosphate, 0.1% Tween, pH 6.8). 100 ml of the antisera were filtered with 0.2 μm, and the column material present was added. For this purpose, the gel was quantitatively rinsed from the column with 10 ml of binding buffer. The incubation was effected overnight at room temperature with swirling. The batches were transferred quantitatively into empty columns (NAP 25, Pharmacia, emptied). The runnings were discarded. The columns were then washed protein-free with 250 ml of binding buffer (protein content of the wash eluate <0.02 A280 nm). Elution buffer was added to the washed columns, and 1 ml fractions were collected. The protein content of each fraction was determined by means of the BCA method (cf. operating instructions of PIERCE, Rockford, Ill., USA). Fractions having protein concentrations >0.8 mg/ml were pooled. After protein determination of the pools by means of the BCA method, yields of 97 mg for the anti-PCT15 antibody 0407-pAk and 60 mg for the anti-PCW14 0410-pAk antibody were obtained.

4. Marking

The anti-PCW14 0410-pAk antibody was treated as follows:

500 μl of the purified antibody were rebuffered in 1 ml of 100 mM potassium phosphate buffer (pH 8.0) according to the operating instructions over an NAP-5 gel filtration column (Pharmacia). The protein concentration determination of the antibody solution gave a value of 1.5 mg/ml.

For chemiluminescence marking of the antibody, 10 μl of MA70 acridinium-NHS-ester (1 mg/ml; from HOECHST Behring) were added to 67 μl of the antibody solution and incubated for 15 minutes at room temperature. Thereafter, 423 μl of 1 M glycine were added and incubation was effected for a further 10 minutes. Thereafter, the marking batch was rebuffered according to operating instructions over an NAP-5 gel filtration column (Pharmacia) in 1 ml of mobile phase A (50 mM potassium phosphate, 100 mM NaCl, pH 7.4) and freed from low molecular weight constituents. A gel filtration HPLC was carried out for separating off final residues of labels not bound to antibodies (column: Waters Protein Pak SW300). The sample was applied and was chromatographed at a flow rate of 1 ml/min with mobile phase A. The wavelengths 280 nm and 368 nm were measured using a flow photometer. The absorption ratio 368 nm/280 nm as a measure of the degree of marking of the antibody was 0.10 at the peak. The fractions containing monomeric antibodies (retention time 8-10 min) were collected, and were collected in 3 ml of 100 mM sodium phosphate, 150 mM NaCl, 5% bovine serum albumin, 0.1% sodium azide, pH 7.4.

5. Coupling

The anti-PCT15 antibody 0407-pAk was treated as follows:

Irradiated 5 ml polystyrene tubes (from Greiner) were coated with purified antibody as follows: the antibody was diluted to a concentration of 6.6 µg/ml in 50 mM Tris, 100 mM NaCl, pH 7.8. 300 µl of this solution were pipetted into each tube. The tubes were incubated for 20 hours at 22° C. The solution was filtered with suction. Each tube was then filled with 4.2 ml of 10 mM sodium phosphate, 2% Karion FP, 0.3% bovine serum albumin, pH 6.5. After 20 hours, the solution was filtered with suction. Finally, the tubes were dried in a vacuum drier.

B. Carrying Out and Evaluating the Immunoassay

An assay buffer of the following composition was prepared: 100 mM sodium phosphate, 150 mM NaCl, 5% bovine serum albumin (BSA), 0.1% unspecified sheep IgG, 0.1% sodium azide, pH 7.4

The above-mentioned chemically synthesized peptide (peptide PSW44) which corresponds to the positions 169-212 of preproendothelin-1 serves as standard material. This was serially diluted in horse normal serum (from SIGMA). Concentrations according to the weight of the peptide taken were ascribed to the standards thus prepared.

Measuring samples were EDTA plasmas of apparently healthy persons, of patients with sepsis and of patients with various cardiovascular diseases.

50 µl of standards or samples and 200 µl of assay buffer were pipetted into the test tubes. Incubation was effected for two hours at 22° C. with shaking. Thereafter, washing was effected 4 times with 1 ml of wash solution (0.1% Tween 20) each time per tube and the latter were allowed to drip off. 200 µl of assay buffer, containing 1 million RLU (relative light units) of the MA70-marked antibody, were then pipetted. Incubation was effected for two hours at 22° C. with shaking. Thereafter, washing was effected 4 times with 1 ml of wash solution (0.1% Tween 20) each time per tube, the latter were allowed to drip off and the chemiluminescence bound to the tube was measured in a luminometer (from BERTHOLD, LB952T; base reagents BRAHMS AG).

Using the MultiCalc software (spline fit), the concentrations of the samples were read from the standard curve.

C. Results

Figure 1:
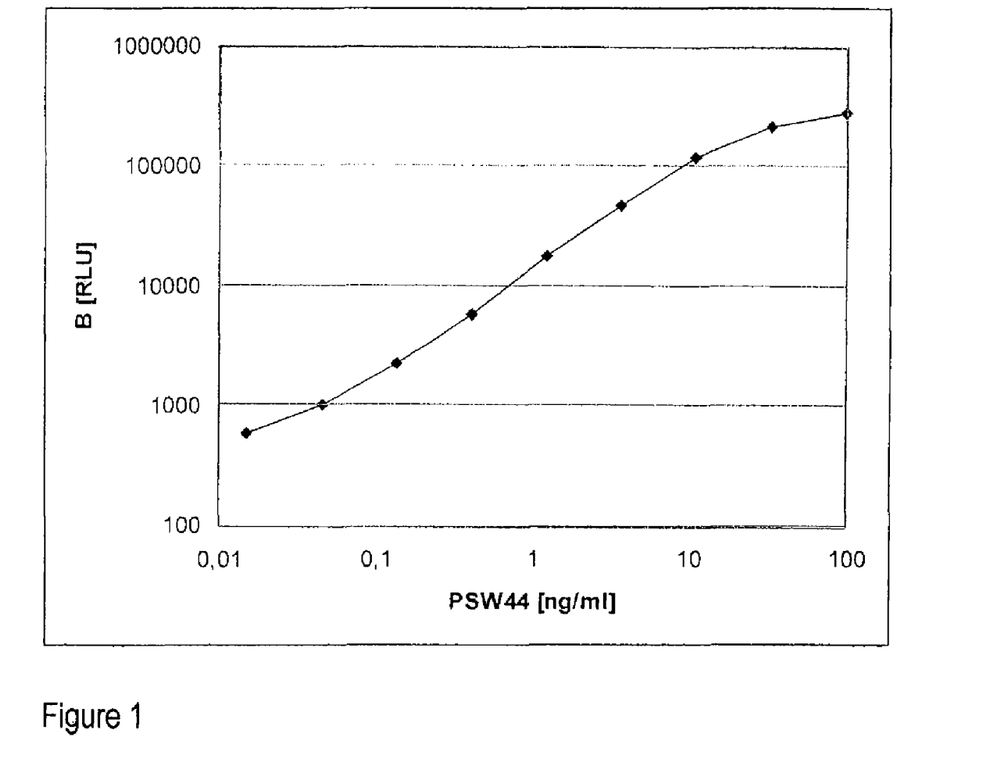
FIG. 1 shows a typical standard curve for the currently preferred sandwich assay with two antibodies which bind to amino acid sequences which correspond to the positions 168-181 and 200-212 of preproendothelin-1, for the determination of a C-terminal proendothelin peptide sequence in human plasma, said sandwich assay being described more exactly in the experimental section.

The analyte measurable using the sandwich immunoassay developed (antibody against the positions 168-181 and 200-212) is referred to below as C-terminal proendothelin or Ct-proendothelin. A typical standard curve for the test developed is shown in FIG. 1. By means of the test, it is also possible to determine Ct-proendothelin concentrations substantially below 50 pg/ml.

Figure 2:
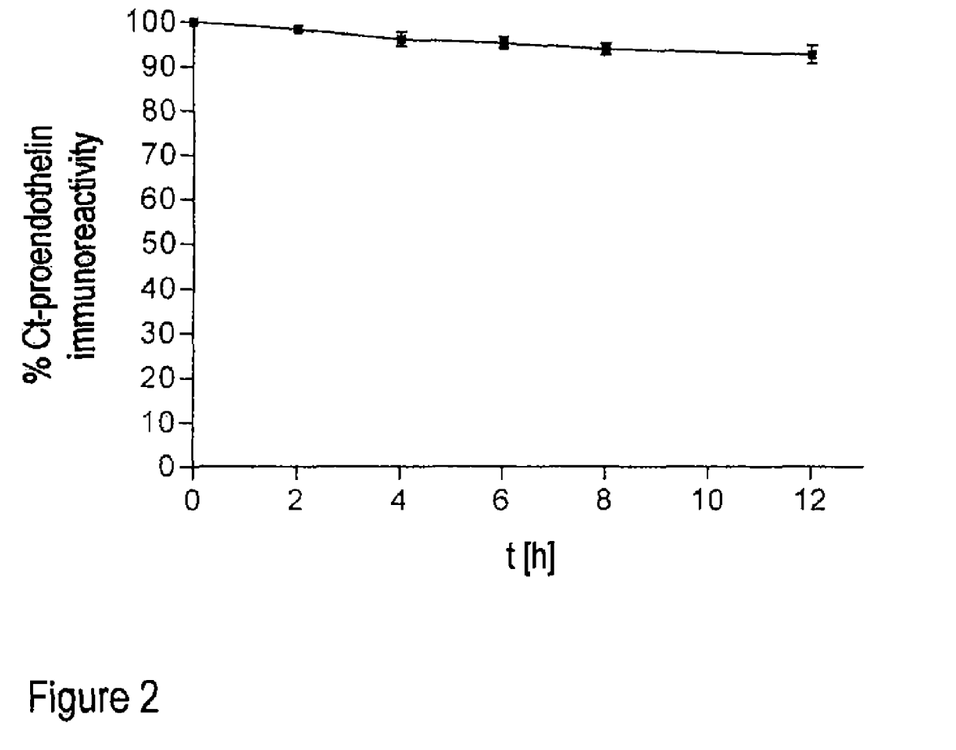
FIG. 2 shows a diagram which shows that, on storage of EDTA plasma samples from septic and cardiological patients at room temperature over 12 hours, no significant loss of immunoreactivity occurs in an assay according to FIG. 1.

In order to examine the question as to whether problems were to be expected in a measurement of the C-terminal peptide fragment owing to insufficient stability in a sample or measuring solution, 5 sepsis plasmas were measured in each case fresh and after storage for 12 hours at room temperature. The results are summarized in FIG. 2. They show that, after storage for 12 days, the immunoreactivity was virtually unchanged at about 93% of the initially measured immunoreactivity. This stability detected is a major advantage for diagnostics from points of view relating to handling.

Figure 3:
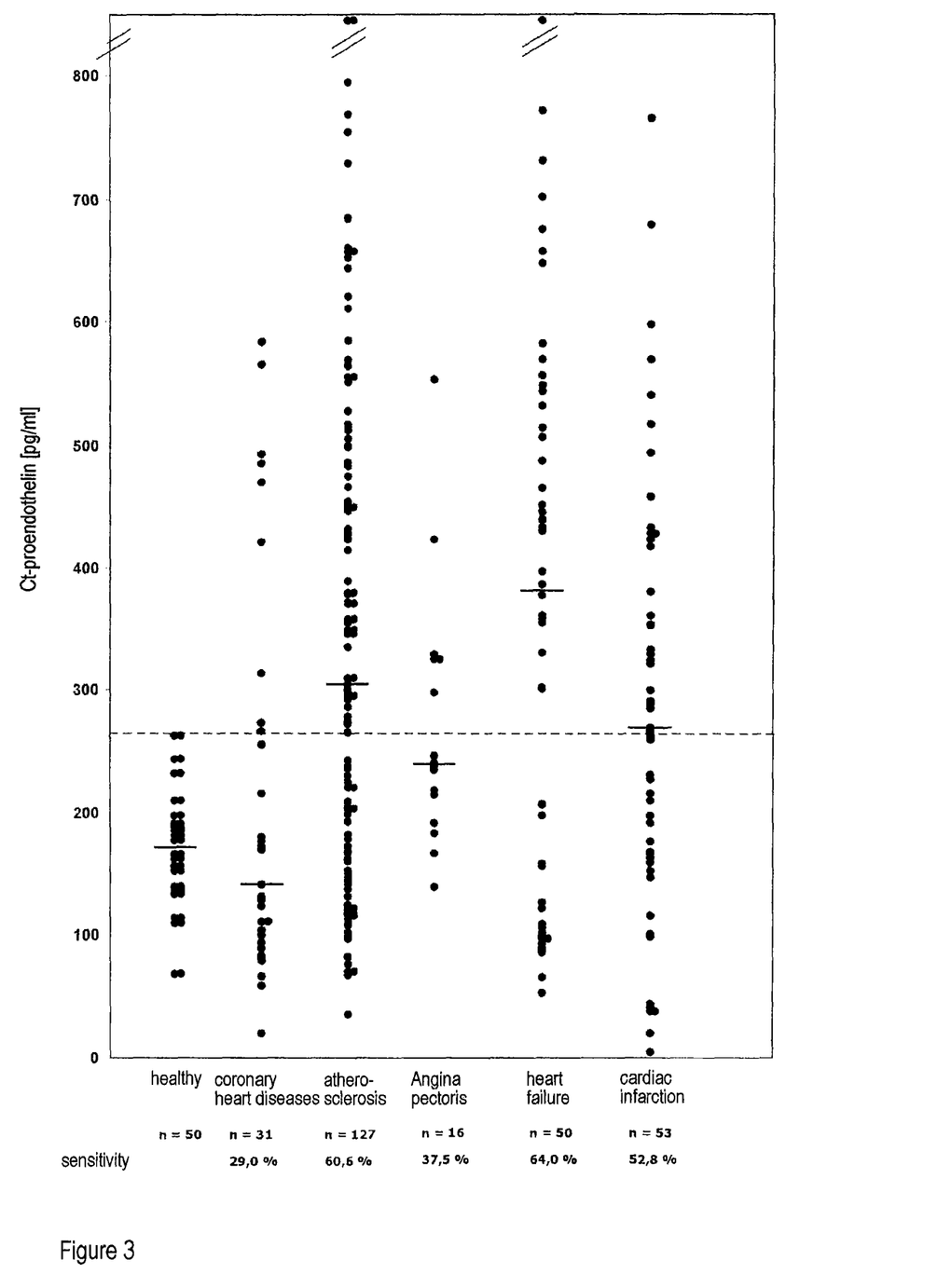
FIG. 3 shows the measurement of plasmas of 5 groups of human patients with different diseases/diagnoses, compared with the measurements for apparently healthy persons; the dotted line indicates the maximum value found in healthy persons (line for 100% specificity, based on healthy controls)
Figure 4:
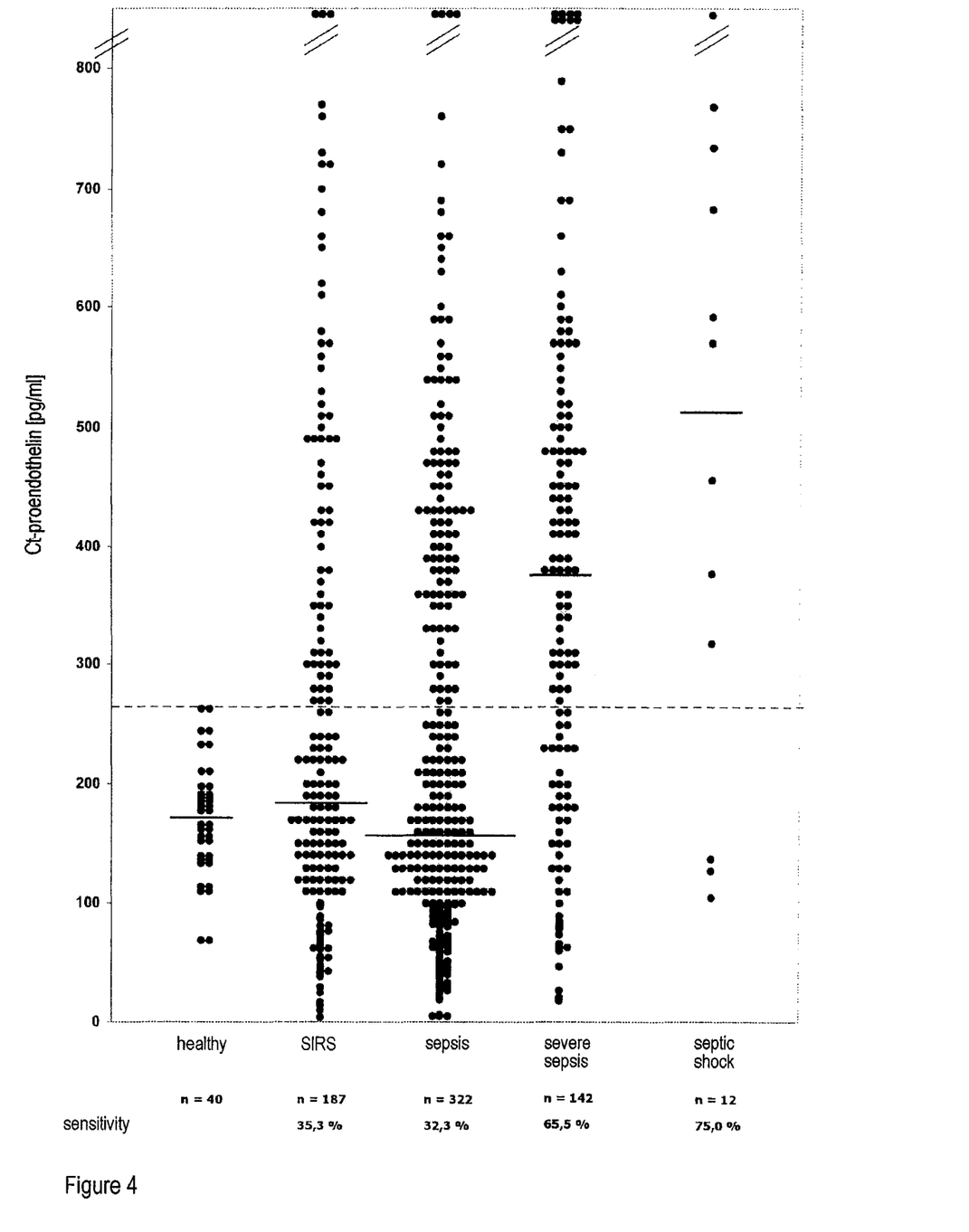
FIG. 4 shows a diagram corresponding to FIG. 3, for four further groups of patient plasmas.

By means of the test, plasmas of cardiological and sepsis patients were measured. The results obtained are shown in FIGS. 3a and 3b. For all cardiological clinical pictures investigated, increased values were found compared with normal controls. Increased values were also found for patients with SIRS (systemic inflammatory response syndrome) and septic conditions. The diagnostic sensitivity (at given 100% specificity, based on healthy controls) increased with the severity of the disease: sepsis 32.3%, severe sepsis 65.5% and septic shock 75%.

When the samples were measured using a modified assay in which one of the antibodies of the above-mentioned sandwich assay was replaced by an antibody which detected the amino acids 184-203 of preproendothelin-1, substantially identical results were obtained, as expected.

On the other hand, when one of the antibodies used recognized an amino acid sequence which is localized more closely to the N-terminus of the preproendothelin (32-52 or 136-148), it was not possible to obtain measured values raised compared with healthy persons. This indicates that proendothelin as such was not present in the plasma samples measured and is not proteolytically processed only with formation of big endothelin, but that the C-terminal sequence 93-212 liberated is also further cleaved, it being necessary for at least one such cleavage point to be present in the range of the amino acids 149-167. The statement applies to the plasmas of patients with the diseases investigated. However, it cannot be ruled out that, for example, the entire C-terminal fragment 93-212 is retained in other patient groups and its selective measurement can deliver diagnostically relevant results.

LIST OF REFERENCES

1. Agapitov A V, Haynes W G. Role of endothelin in cardiovascular disease. J Renin Angiotensin Aldosterone Syst 2002; 3:1-15
2. Arun C, Swift B, Porter K E, West K P, London N J, Hemingway D M. The role of big endothelin-1 in colorectal cancer. Int J Biol Markers 2002; 17:268-74
3. Asham E H, Loizidou M, Taylor I. Endothelin-1 and tumour development. Eur J Surg Oncol 1998; 24:57-60
4. Aubin P, Le Brun G, Moldovan F, Vilette J M, Créminon C, Dumas J, Homyrda L, Soliman H, Azizi M, and Fiet J, Sandwich-type enzyme immunoassay for big endothelin-1 in plasma: concentrations in healthy human subjects unaffected by sex or posture, Clin Chem 43:1, 64-70 (1997)
5. Corder R, Vane J R. Radioimmunoassay evidence that the pressor effect of big endothelin-1 is due to local conversion to endothelin-1. Biochem Pharmacol 1995; 49:375-80
6. de Nucci G, Thomas R, D'Orleans-Juste P, Antunes E, Walder C, Warner T D, Vane J R. Pressor effects of circulating endothelin are limited by its removal in the pulmonary circulation and by the release of prostacyclin and endothelium-derived relaxing factor. Proc Natl Acad Sci USA 1988; 85:9797-800
7. Goraca A. New views on the role of endothelin (minireview). Endocr Regul 2002; 36:161-7
8. Haug C, Koenig W, Hoeher M, Kochs M, Hombach V, Gruenert A, and Osterhues H, Direct enzyme immunometric measurement of plasma big endothelin-1 concentrations and correlation with indicators of left ventricular function. Clin Chem 44:2 239-243 (1998)
9. Haynes W G, Webb D J. Contribution of endogenous generation of endothelin-1 to basal vascular tone. Lancet 1994; 344:852-4
10. Hemsen A, Ahlborg G, Ottosson-Seeberger A, Lundberg J M. Metabolism of Big endothelin-1 (1-38) and (22-38) in the human circulation in relation to production of endothelin-1 (1-21). Regul Pept 1995; 55:287-97
11. Hirata Y, Mitaka C, Emori T, Amaha K, Marumo F. Plasma endothelins in sepsis syndrome. Jama 1993; 270: 2182

12. Iskit A B, Guc O. Effects of endothelin and nitric oxide on organ injury, mesenteric ischemia, and survival in experimental models of septic shock. Acta Pharmacol Sin 2003; 24:953-7
13. Lerman A, Edwards B S, Hallett J W, Heublein D M, Sandberg S M, Burnett J C, Jr. Circulating and tissue endothelin immunoreactivity in advanced atherosclerosis. N Engl J Med 1991; 325:997-1001
14. Mathew V, Lerman A. Clinical implications of a sandwich enzyme immunoassay for big endothelin-1. Clin Chem 1997; 43:9-10
15. Nelson J B, Hedican S P, George D J, Reddi A H, Piantadosi S, Eisenberger M A, Simons J W. Identification of endothelin-1 in the pathophysiology of metastatic adenocarcinoma of the prostate. Nat Med 1995; 1:944-9
16. Pittet J F, Morel D R, Hemsen A, Gunning K, Lacroix J S, Suter P M, and Lundberg J M, Elevated Plasma Endothelin-1 Concentrations Are Associated with the Severity of Illness in Patients with Sepsis. Ann. Surg., Vol. 213, No. 3, 261-264 (1991)
17. Rossi G P, Seccia T M, Albertin G, Pessina A C. Measurement of endothelin: clinical and research use. Ann Clin Biochem 2000; 37 (Pt 5):608-26
18. Shankar A, Loizidou M, Aliev G, Fredericks S, Holt D, Boulos P B, Burnstock G, Taylor I. Raised endothelin 1 levels in patients with colorectal liver metastases. Br J Surg 1998; 85:502-6
19. Sokolovsky M, Endothelins and Sarafotoxins: Receptor Heterogeneity (Minireview); Int. J. Biochem. Vol. 26, No. 3, 335-340, 1994
20. Stewart D J, Kubac G, Costello K B, Cernacek P. Increased plasma endothelin-1 in the early hours of acute myocardial infarction. J Am Coll Cardiol 1991; 18:38-43
21. Stewart D J, Levy R D, Cernacek P, Langleben D. Increased plasma endothelin-1 in pulmonary hypertension: marker or mediator of disease? Ann Intern Med 1991; 114:464-9
22. Tschaikowsky K, Sagner S, Lehnert N, Kaul M, Ritter J. Endothelin in septic patients: effects on cardiovascular and renal function and its relationship to proinflammatory cytokines. Crit Care Med 2000; 28:1854-60
23. Voerman H J, Stehouwer C D, van Kamp G J, Strack van Schijndel R J, Groeneveld A B, Thijs L G. Plasma endothelin levels are increased during septic shock. Crit Care Med 1992; 20:1097-101
24. Wanecek M, Weitzberg E, Rudehill A, Oldner A. The endothelin system in septic and endotoxin shock. Eur J Pharmacol 2000; 407:1-15
25. Wei C M, Lerman A, Rodeheffer R J, McGregor C G, Brandt R R, Wright S, Heublein D M, Kao P C, Edwards W D, Burnett J C, Jr. Endothelin in human congestive heart failure. Circulation 1994; 89:1580-6
26. Weitzberg E, Lundberg J M, and Rudehill A, Elevated Plasma Levels of Endothelin in Patients With Sepsis Syndrome. Circulatory Shock 33:222-227 (1991)
27. Yanagisawa M, Kurihara H, Kimura S, Tomobe Y, Kobayashi M, Mitsui Y, Yazaki Y, Goto K, Masaki T. A novel potent vasoconstrictor peptide produced by vascular endothelial cells. Nature 1988; 332:411-5

---

The invention claimed is:

1. An in vitro method for the determination of the formation of endothelins in a human patient suspected of a disease selected from the group consisting of cardiovascular disease, and sepsis, wherein the formation of endothelin-1 (SEQ ID NO.:2) and big endothelin-1 (SEQ ID NO.: 3) is determined by detecting a C-terminal fragment of preproendothelin-1 (SEQ ID NO.: 1), the method comprising:
   obtaining a whole blood, plasma or serum sample from the patient;
   contacting said sample with first antibodies that specifically bind to a first peptide within amino acids 168-212 of preproendothelin-1 (SEQ ID NO.: 1) and second antibodies that specifically bind to a second peptide within amino acids 168-212 of preproendothelin-1, one of said first and second antibodies being labeled with a detectable marker, wherein the level of said C-terminal fragment detected by said first and second antibodies correlates with the level of formation of endothelin-1 (SEQ ID NO:2) or big endothelin-1 (SEQ ID NO:3) in said patient.

2. The method of claim 1, wherein said first and second antibodies bind to two different peptides of preproendothelin-1 selected from peptides consisting of amino acids 168-181, 184-203 and 200-212 of preproendothelin-1.

3. The method of claim 1, wherein said method provides for the quantitative or semiquantitative determination of the C-terminal fragment of preproendothelin-1 comprising amino acids 168-212 of preproendothelin-1.

4. The method as claimed in claim 3, wherein said determination is an immunochromatographic point-of-care test.

5. The method as claimed in claim 1, wherein the first and second antibodies used for the determination are selected from monoclonal antibodies, affinity-purified polyclonal antibodies, or a combination of monoclonal and affinity-purified antibodies.

6. The method as claimed in claim 1, wherein the first and second antibodies are obtained by immunizing an animal with a synthetic peptide consisting of amino acids 168-181, 184-203 or 200-212 of preproendothelin-1.

7. The method as claimed in claim 1, wherein one of said first and second antibodies is bound to a solid phase.

8. The method as claimed in claim 1, wherein said first and second antibodies are present in dispersed form in a liquid reaction mixture, a first detectable marker being bound to the first antibody, and a second detectable marker being bound to the second antibody so that, after binding of both antibodies to the terminal fragment of preproendothelin-1 to be detected to form an analyte/antibody complex, a measurable signal which permits detection of the complexes in the measuring solution is generated.

9. The method as claimed in claim 8, wherein the detectable marker comprises rare earth cryptates or chelates in combination with a fluorescent or chemiluminescent dye.

10. The method as claimed in claim 1, wherein said disease is sepsis.

11. The method as claimed in claim 10, which is carried out as part of a multiparameter determination, in which at least one further parameter relevant to sepsis diagnosis is determined simultaneously.

12. The method as claimed in claim 11, wherein the further parameter or parameters relevant for sepsis diagnosis is or are selected from the group which consists of anti-ganglioside antibodies, the proteins calcitonin, CA 125, CA 19-9, S100B, S100A proteins, LASP-1, soluble cytokeratin fragments, in particular CYFRA 21, TPS and/or soluble cytokeratin-1 fragments (sCY1F), the peptides inflammin and CHP, fragments of the prohormones pro-ANP, pro-BNP or pro-ADM, glycine-N-acyltransferase (GNAT), carbamoylphosphate synthetase 1 (CPS 1) and C-reactive protein (CRP) or fragments thereof.

13. The method as claimed in claim 1, wherein said cardiovascular disease is selected from the group consisting of atherosclerosis, heart failure, cardiac infarction and pulmonary arterial hypertension.

14. The method as claimed in claim 13, which is carried out as part of a multiparameter determination, in which further parameters relevant to cardiovascular disease are determined simultaneously.

15. A method for determining the level of endothelin-1 formation in a human patient suspected of a disease selected from the group consisting of cardiovascular disease and sepsis, wherein the level of endothelin-1 formation is determined by measuring the level of a C-terminal fragment of preproendothelin-1 (SEQ ID NO.: 1), the method comprising:
   obtaining a whole blood, plasma or serum sample from the patient;

contacting said sample with first antibodies that specifically bind to a first peptide within amino acids 168-212 of preproendothelin-1 (SEQ ID NO.: 1) and second antibodies that specifically bind to a second peptide within amino acids 168-212 of preproendothelin-1, one of said first and second antibodies being labeled with a detectable marker; and measuring the level of the C-terminal fragment of pre-proendothelin-1 detected by said first and second antibodies, wherein the level of C-terminal fragment detected by said first and second antibodies correlates with the level of endothelin-1 formation in said patient.

* * * * *

UNITED STATES PATENT AND TRADEMARK OFFICE
CERTIFICATE OF CORRECTION

| | | |
|---|---|---|
| PATENT NO. | : 8,124,366 B2 | Page 1 of 1 |
| APPLICATION NO. | : 10/588746 | |
| DATED | : February 28, 2012 | |
| INVENTOR(S) | : Bergmann et al. | |

It is certified that error appears in the above-identified patent and that said Letters Patent is hereby corrected as shown below:

Title page;

In the Assignee (73): Delete "B.R.A.H.M.S. GmbH" and insert -- B.R.A.H.M.S GmbH --

Signed and Sealed this
Tenth Day of July, 2012

David J. Kappos
*Director of the United States Patent and Trademark Office*

SEQUENCE LISTING

```
<160> NUMBER OF SEQ ID NOS: 7

<210> SEQ ID NO 1
<211> LENGTH: 212
<212> TYPE: PRT
<213> ORGANISM: Homo sapiens

<400> SEQUENCE: 1

Met Asp Tyr Leu Leu Met Ile Phe Ser Leu Leu Phe Val Ala Cys Gln
  1               5                  10                  15

Gly Ala Pro Glu Thr Ala Val Leu Gly Ala Glu Leu Ser Ala Val Gly
             20                  25                  30

Glu Asn Gly Gly Glu Lys Pro Thr Pro Ser Pro Pro Trp Arg Leu Arg
         35                  40                  45

Arg Ser Lys Arg Cys Ser Cys Ser Ser Leu Met Asp Lys Glu Cys Val
     50                  55                  60

Tyr Phe Cys His Leu Asp Ile Ile Trp Val Asn Thr Pro Glu His Val
 65                  70                  75                  80

Val Pro Tyr Gly Leu Gly Ser Pro Arg Ser Lys Arg Ala Leu Glu Asn
                 85                  90                  95

Leu Leu Pro Thr Lys Ala Thr Asp Arg Glu Asn Arg Cys Gln Cys Ala
            100                 105                 110

Ser Gln Lys Asp Lys Lys Cys Trp Asn Phe Cys Gln Ala Gly Lys Glu
        115                 120                 125

Leu Arg Ala Glu Asp Ile Met Glu Lys Asp Trp Asn Asn His Lys Lys
    130                 135                 140

Gly Lys Asp Cys Ser Lys Leu Gly Lys Lys Cys Ile Tyr Gln Gln Leu
145                 150                 155                 160
```

```
Val Arg Gly Arg Lys Ile Arg Ser Ser Glu Glu His Leu Arg Gln
            165                 170                 175

Thr Arg Ser Glu Thr Met Arg Asn Ser Val Lys Ser Phe His Asp
        180                 185                 190

Pro Lys Leu Lys Gly Lys Pro Ser Arg Glu Arg Tyr Val Thr His Asn
    195                 200                 205

Arg Ala His Trp
    210

<210> SEQ ID NO 2
<211> LENGTH: 21
<212> TYPE: PRT
<213> ORGANISM: Homo sapiens

<400> SEQUENCE: 2

Cys Ser Cys Ser Ser Leu Met Asp Lys Glu Cys Val Tyr Phe Cys His
  1               5                  10                  15

Leu Asp Ile Ile Trp
            20

<210> SEQ ID NO 3
<211> LENGTH: 38
<212> TYPE: PRT
<213> ORGANISM: Homo sapiens

<400> SEQUENCE: 3

Cys Ser Cys Ser Ser Leu Met Asp Lys Glu Cys Val Tyr Phe Cys His
  1               5                  10                  15

Leu Asp Ile Ile Trp Val Asn Thr Pro Glu His Val Val Pro Tyr Gly
            20                  25                  30

Leu Gly Ser Pro Arg Ser
        35

<210> SEQ ID NO 4
<211> LENGTH: 15
<212> TYPE: PRT
<213> ORGANISM: Artificial Sequence
<220> FEATURE:
<223> OTHER INFORMATION: Description of Artificial Sequence: Partial EN1
      Sequence with terminal C

<400> SEQUENCE: 4

Cys Arg Ser Ser Glu Glu His Leu Arg Gln Thr Arg Ser Glu Thr
  1               5                  10                  15

<210> SEQ ID NO 5
<211> LENGTH: 14
<212> TYPE: PRT
<213> ORGANISM: Artificial Sequence
<220> FEATURE:
<223> OTHER INFORMATION: Description of Artificial Sequence: Partial EN1
      sequence with terminal C

<400> SEQUENCE: 5

Cys Ser Arg Glu Arg Tyr Val Thr His Asn Arg Ala His Trp
  1               5                  10

<210> SEQ ID NO 6
<211> LENGTH: 20
<212> TYPE: PRT
<213> ORGANISM: Artificial Sequence
<220> FEATURE:
<223> OTHER INFORMATION: Description of Artificial Sequence: Partial EN1
      sequence with terminal C
```

```
-continued

<400> SEQUENCE: 6

Asn Ser Val Lys Ser Ser Phe His Asp Pro Lys Leu Lys Gly Lys Pro
  1               5                  10                  15

Ser Arg Glu Arg
             20

<210> SEQ ID NO 7
<211> LENGTH: 44
<212> TYPE: PRT
<213> ORGANISM: Homo sapiens

<400> SEQUENCE: 7

Ser Ser Glu Glu His Leu Arg Gln Thr Arg Ser Glu Thr Met Arg Asn
  1               5                  10                  15

Ser Val Lys Ser Ser Phe His Asp Pro Lys Leu Lys Gly Lys Pro Ser
                 20                  25                  30

Arg Glu Arg Tyr Val Thr His Asn Arg Ala His Trp
             35                  40
```